United States Patent
Tsutsumi et al.

(10) Patent No.: US 6,274,571 B1
(45) Date of Patent: Aug. 14, 2001

(54) AGENT FOR PREVENTING AND CURING FATTY LIVER AND METHOD FOR CURING THEREOF

(75) Inventors: Kazuhiko Tsutsumi, Tokushima; Yasuhide Inoue, Naruto, both of (JP)

(73) Assignee: Otsuka Pharmaceutical Factory, Inc., Tokushoma-ken (JP)

( * ) Notice: Subject to any disclaimer, the term of this patent is extended or adjusted under 35 U.S.C. 154(b) by 0 days.

(21) Appl. No.: 09/582,765

(22) PCT Filed: Feb. 16, 1999

(86) PCT No.: PCT/JP99/00652

§ 371 Date: Jun. 30, 2000

§ 102(e) Date: Jun. 30, 2000

(87) PCT Pub. No.: WO99/40923

PCT Pub. Date: Aug. 19, 1999

(30) Foreign Application Priority Data

Feb. 17, 1998 (JP) .................................... 10-052884

(51) Int. Cl.[7] ............................. A61K 31/662; A61P 1/16
(52) U.S. Cl. .............................. 514/113; 558/192
(58) Field of Search ............................ 514/113; 558/192

(56) References Cited

U.S. PATENT DOCUMENTS 4,822,780    4/1989    Tsuda et al. ........................... 514/119

FOREIGN PATENT DOCUMENTS 0 402 033 B1    10/1995    (EP) .................................... C07F/9/40
61-151199    7/1986    (JP) .................................... C07F/9/40
3-68592    3/1991    (JP) .................................... C07F/9/40
10-265387    10/1998    (JP) ................................. A61K/31/66

OTHER PUBLICATIONS

The Merck Manual of Diagnosis and Therapy. Seventeenth Edition. Merck & Co., Inc., 1999. Mark H. Beers, M.D., and Robert Berkow, M.D., eds; Internet Edition, Section 4, Chapter 39. http://www.merck.com/pubs/mmanual/section4/chapter39/39a.htm.*

JP Patent Abstract, 10265387, Oct. 6, 1998.

* cited by examiner

*Primary Examiner*—Michael G. Ambrose
(74) *Attorney, Agent, or Firm*—Sughrue, Mion, Zinn, Macpeak & Seas

(57) ABSTRACT

The present invention provides an agent for preventing and curing fatty liver containing, as the effective ingredient compound, a carboxylic acid amide derivative represented by the general formula (1),

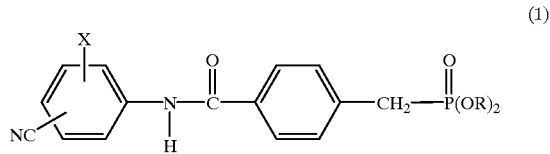

(1)

(wherein R is a lower alkyl group; and X is a halogen atom), and a method for curing fatty liver by administering said agent.

4 Claims, 2 Drawing Sheets

(1 of 2 Drawing Sheet(s) Filed in Color)

AGENT FOR PREVENTING AND CURING FATTY LIVER AND METHOD FOR CURING THEREOF

TECHNICAL FIELD

The present invention relates to an agent for preventing and curing fatty liver and to a method for curing thereof.

BACKGROUND ART

Fatty liver is a diseased state of the liver wherein lipids, mainly neutral fats (triglycerides, TG) are accumulated excessively in the liver, thus fatty vacuoles are observed in about more than a half number of the liver cells. As to the cause of fatty liver, there are reported various pathogenics such as obesity, diabetes mellitus, alcoholic intake, oxygen deficit, endocrinic disorder, exogenic toxins or medicines, endogenous toxins and the like. Particularly, along the recent trend on increasing of obesity, a number of patients with supervenient fatty liver are also increasing. Said fatty liver is necessarily treated at the early stage, because after all this disease may be migrated to severe hepatopathies, such as hepatitis, hepatic cirrhosis and the like, finally such instances are not seldom to court death. However, at the present, an agent effective for curing fatty liver has not been known yet, and dietetic therapy is only known as a general therapy. Thus development of a medicine capable to prevent and cure fatty liver satisfactorily and effectively is earnestly desired.

Heretofore, the present inventors have conducted an extensive research work regarding effective ingredient compounds used for pharmaceuticals. Then in the course of research work, previously the inventors have found the fact that a series of carboxylic acid amide derivatives are effective as antiinflammatory agent and calcium antagonistic agent, then invention relating to said derivatives was completed and patent applications were filed (JP-A-61-151199 and EP-A-273444).

Further, the present inventors have additionally found the fact that other carboxylic acid amide derivatives relating to the above-mentioned carboxylic acid amide derivatives have excellent activity for lowering lipids, and are excellent in low toxicity regarding side-effects etc., thus the latter carboxylic acid amide derivatives are useful agents for curing hyperlipidemia, and also for preventing and curing various diseases (hyperlipidemia), such as hypercholesteremia, hypertriglyceridemia, hyperphospholipidemia, hyper-free fatty acidemia and the like. Then an invention on the basis of such finding was filed as a patent application (Japanese Patent No. 2584336).

Additionally, the present inventors have found the facts that, other than the useful activity for curing hyperlipidemia, the above-mentioned carboxylic acid amide derivatives also have activity for inhibiting excretion of proteinurea, thus these derivatives are effective as agents for curing nephritis, then an invention on the basis of such finding was filed as a patent application (Japanese Patent Application Hei 9-93002).

DISCLOSURE OF THE INVENTION

An object of the present invention is to develop novel pharmaceutical applications of the above-mentioned carboxylic acid amide derivatives by using their excellent properties such as low toxicities. Particularly the present invention is aimed to provide an agent for preventing and curing fatty liver and method for curing thereof.

The present inventors have conducted an extensive research work followed by the above-mentioned object. As the result, regardless of the excellent pharmaceutical applications for curing hyperlipidemia and nephritis performed by the above-mentioned compound, unexpectedly the inventors have found novel knowledges from the above-mentioned pharmacological activities, that the above-mentioned carboxylic acid amide derivatives have activities for lowering neutral fats (triglycerides, TG) and total cholesterols in the liver, also effective for preventing and curing fatty liver. Thus, the present invention was completed on the basis of said novel knowledges.

MEANS FOR SOLVING THE PROBLEM

The present invention relates to an agent for preventing and curing fatty liver containing, as the effective ingredient, a carboxylic acid amide derivative represented by the general formula (1),

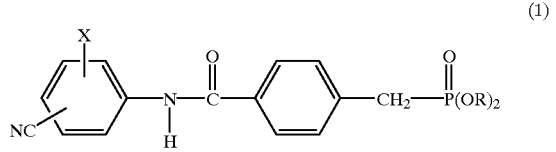

(wherein R is a lower alkyl group; and X is a halogen atom), and to a method for curing thereof by administering said agent.

As explained previously, the carboxylic acid amide compound represented by the above-mentioned general formula (1), which is contained as the effective ingredient in the agent for preventing and curing fatty liver and method for curing fatty liver according to the present invention, possesses activity for lowering neutral fats (triglycerides, TG) and cholesterols in the blood. Therefore, said compound is known as effective for curing hyperlipidemia by the present inventors (JP-A-3-68592). However, such activity is understood rather contrary to the activity for inhibiting accumulation of neutral fats in the liver or lowering cholesterols in the liver for preventing and curing fatty liver.

In fact, among compounds having activity for lowering neutral fats and cholesterols in the blood and used as agents for curing hyperlipidemia, for example "clofibrate", it is known to cause accumulation of neutral fats in the liver as a side-effect and induces hepatomegaly (cf., e.g., JP-A-8-119860).

On the basis of such findings, the present invention was completed surprisingly and contrary to the previous knowledge, although the compound represented by the above-mentioned general formula (1) possesses activity for lowering neutral fats and cholesterols in the blood, said compound also possesses activity for inhibiting both accumulation of fats in the liver and activity for lowering cholesterols in the liver, thus the compound performs desired effects for preventing and curing fatty liver.

BRIEF DESCRIPTION OF DRAWINGS

The file of this patent contains at least one drawing executed in color. Copies of this patent with color drawing(s) will be provided by the Patent and Trademark Office upon request and payment of the necessary fee.

FIG. 1 shows monochrome picture (black and white) and FIG. 2 shows color picture.

BEST MODE FOR CARRYING OUT THE INVENTION

Figure 1:
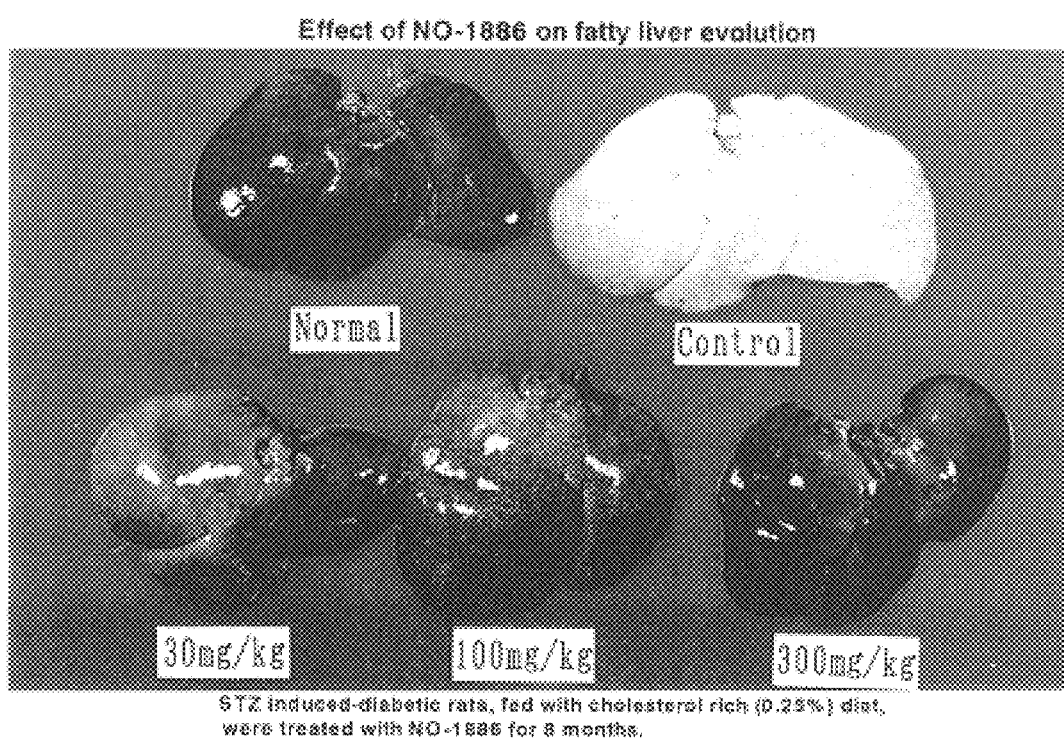
FIG. 1 and FIG. 2 are substitute photographs for figures and show states of the livers enuclated from the rats of each one of test groups in accordance with Pharmacological test-4.

In the general formula (1) representing the effective ingredient compound of the present invention, as to the lower alkyl group represented by R, there can be exemplified a straight chain and branched chain alkyl groups having 1 or 6 carbon atoms, for example methyl, ethyl, propyl, isopropyl, butyl, t-butyl, pentyl, hexyl groups and the like; and as to the halogen atom represented by X, there can be involved a fluorine atom, a chlorine atom, a bromine atom and an iodine atom.

Particularly, as to the above-mentioned effective ingredient compounds capable to perform excellent activity for preventing and curing fatty liver, there can be exemplified carboxylic acid amide derivatives represented by the following general formulas (1a) and (1b), wherein CN group as a substituent in the phenyl ring is bonded to the ortho-position or para-position relative to the amino group as the substituent, further the halogen atom represented by X is bonded to the para-position or ortho-position in the phenyl ring.

General Formula (1a)

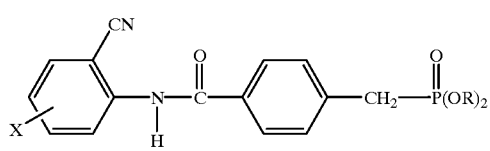

(wherein R and X are the same as defined in the above).

General Formula (1b)

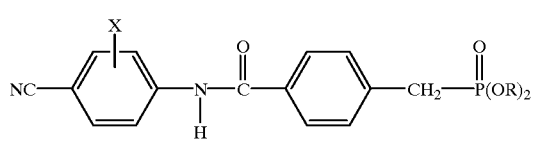

(wherein R and X are the same as defined in the above).

Among these effective ingredient compounds represented by the above-mentioned general formula (1a), diethyl 4-[N-(4-bromo-2-cyanophenyl)carbamoyl]benzylphosphonate can be exemplified, because it can perform the best effect for preventing and curing fatty liver.

In addition to the excellent effects for preventing and curing fatty liver, the carboxylic acid amide derivatives represented by the above-mentioned general formula (1), particularly derivatives represented by the general formula (1a) and the general formula (1b) possess excellent features of the safety without having adverse effects, such as hemolysis, from these reasons they are quite useful agents for preventing and curing fatty liver. Further, the above-mentioned derivatives possess features without having side-effects to the liver, for example hepatomegaly due to the accumulation of lipids in the liver and edema, thus from these reasons, they are particularly useful as agents for preventing and curing fatty liver.

In the present invention, the carboxylic acid amide derivatives as the effective ingredient can be prepared by various methods. For example, Japanese Patent No. 2584336 can be cited. Particularly, there can be exemplified by reacting a carboxylic acid chloride derivative, corresponding to the desired compound of the above-mentioned general formula (1), with an amine corresponding to the objective compound of the above-mentioned general formula (1), having a halogen atom and cyano group as substituents in the phenyl ring, in a suitable solvent such as an aromatic or aliphatic hydrocarbon or halogenated hydrocarbon, in the presence of a deacidifying agent, for example a tertiary amine such as triethylamine or the like, at room temperature to refluxing temperature of the solvent, for about 0.5 to 10 hours.

The above-mentioned effective ingredient compound represented by the general formula (1) is formulated as in the form of general pharmaceutical preparations and to make as agents for preventing and curing fatty liver of the present invention. Said pharmaceutical preparations are generally formulated with commonly used diluents, such as fillers, bulking agents, binders, wetting agents, disintegrating agents, surface active agents, lubricants and the like; or excipients.

The pharmaceutical preparations can be selected from various administration forms in accordance with the therapeutic purposes, and typical administration forms can be exemplified tablets, pills, powders, liquids, suspensions, emulsions, granules, capsules, suppositories, injection preparations (liquids, suspensions, etc.) and the like.

In case of shaping the administration unit form into tablets, various carriers which are well-known in this field can be selected from a wide range and used. Examples of the carriers are, excipients such as lactose, white sugar, sodium chloride, glucose, urea, starch, calcium carbonate, kaolin, crystalline cellulose, silicic acid and the like; binders such as water, ethanol, propanol, simple syrup, glucose solution, starch solution, gelatin solution, carboxymethyl cellulose, shellac, methyl cellulose, potassium phosphate, polyvinylpyrrolidone and the like; disintegrating agents such as carboxymethyl cellulose or its calcium salt, microcrystalline cellulose, sodium alginate, agar powder, laminaran powder, sodium hydrogen-carbonate, calcium carbonate, fatty acid esters of polyoxyethylene sorbitan, sodium laurylsulfate, mono-glyceride of stearic acid, starch, lactose and the like; disintegration inhibitors such as white sugar, stearin, cacao butter, hydrogenated oils and the like; absorption accelerators, such as quaternary ammonium salts, sodium laurylsulfate and the like; wetting agents such as glycerin, starch and the like; adsorbents such as starch, lactose, kaolin, bentonite, colloidal silicic acid and the like; and lubricants such as refined talc, stearates, boric acid powder, polyethylene glycols and the like. Further, the tablet preparations can be shaped into tablets coated with usual tablet coatings, for example sugar coated tablets, gelatin film coated tablets, tablets coated with enteric coating, tablets coated with film coating, or double layer tablets and multiple layer tablets.

In case of shaping the administration unit form into pills, carriers for example excipients such as glucose, lactose, starch, cacao butter, hydrogenated vegetable oils, kaolin, talc and the like; binders such as arabic gum powder, tragacnth powder, gelatin, ethanol and the like; and disintegrating agents such as laminaran, agar and the like can be used.

In case of shaping the administration unit form into suppositories, carriers such as polyethylene glycols, cacao butter, higher alcohols, esters of higher alcohols, gelatin, semi-synthesized glycerides and the like can be used.

Capsule preparations are generally prepared in accordance with a common method by mixing the carboxylic acid amide compound of the present invention with the above-mentioned various carriers, then thus obtained mixture is filled into hard capsules, soft capsules and the like.

In case of shaping the administration unit form into injection preparations, liquid preparations, emulsion preparations and suspension preparations, those are sterilized, further these preparations may be preferably isotonic to the blood. In case of shaping these preparations, diluents such as water, ethyl alcohol, macrogols, propylene glycols, ethoxylated isostearyl alcohol, polyoxylated isostearyl alcohol, fattyl acid esters of polyoxyethylene sorbitan and the like can be used. For the purpose to prepare isotonic injection preparations, adequate amounts of sodium chloride, glucose or glycerin may be added to the injection preparations, further, common dissolving additives, buffering agents, local anesthetics and the like may also be added.

Moreover, if necessary, coloring agents, preservatives, spices, flavors, sweetening agents and other medicines may be added to the objective pharmaceutical preparations of the present invention.

Amount of the effective ingredient compound to be contained in the pharmaceutical preparations of the present invention is not specifically restricted and can be selected from a wide range, generally 1 to 70% by weight of the effective ingredient may be contained in the objective pharmaceutical preparation.

Methods for administering pharmaceutical preparation of the present invention are not specifically restricted, they can be determined in accordance with various forms of pharmaceutical preparations, age of the patient, distinction of sex and other conditions, the degree of symptom and the like. For example, tablets, pills, liquids, suspensions, emulsions, granules and capsules are administered orally. While, injection preparations are intravenously administered singly or by mixing with common transfusions such as glucose or amino acid solutions, and if necessary, they are singly administered intramuscularly, intracutaneously, subcutaneously or intraperitoneally. Suppositories are administered to the rectum.

Dosage of pharmaceutical preparation of the present invention is suitably selected depend on the usage age of the patient, distinction of sex and other conditions, the degree of symptom and the like, generally amount of the effective ingredient compound may be about 450 mg to 4.5 g/kg of the body weight of an adult per day, and the pharmaceutical preparation can be administered dividedly in 1 to 4 times a day.

EXAMPLES

The present invention will be explained in detail by illustrating with Preparation examples and Pharmacological test examples. Further, Pharmaceutical preparation examples of agents for preventing and curing fatty liver of the present invention will be disclosed.

Preparation Example 1

3.94 Grams (20 millimoles) of 2-amino-5-bromo-benzonitrile, 2.22 g (22 millimoles) of triethylamine and 0.49 g (4 millimoles) of 4-dimethylaminopyridine were dissolved in 40 ml of dry dichloromethane, under ice-cooling there was added dropwise slowly 40 ml of dry dichloromethane solution of 5.81 g (20 millimoles) of 4-diethoxyphosphorylmethylbenzoyl chloride with stirring. The reaction was carried out at room temperature for 10 hours, to this reaction mixture was added 50 ml of water, then extracted with chloroform and the organic layer was dried over anhydrous sodium sulfate, next the solvent was removed by distillation under reduced pressure. Thus obtained residue was refined by means of a silica gel column chromatography (eluted with chloroform: ethyl acetate= 1:2), recrystallized from benzen-n-hexane, there was obtained 2.94 g of diethyl 4-[N-(4-bromo-2-cyanophenyl)carbamoyl]benzylphosphonate as colorless crystals.

Melting point: 165–166° C. (recrystallized from benzene-n-hexane).

Pharmacological Test-1

[Test of the effect for inhibiting and improving fatty liver]

Male rats of age in 9 months (SD strain rats, average body weight: 700 g) were classified into 3 groups, one of them (normal group: consisting of 9 rats) were kept by feeding with solid feed CRF-1 (manufactured by Oriental Yeast Co., Ltd.) for 3 months.

Other two of them (test group of the present invention consisting of 6 rats; and control group consisting of 6 rats) were kept, respectively by feeding with solid feed CRF-1 (manufactured by Oriental Yeast Co., Ltd.) and containing 26.7% of safflower oil for 3 months.

In the test group of the present invention, the rats were kept with the above-mentioned solid feed and at the same time diethyl 4-[N-(4-bromo-2-cyanophenyl)carbamoyl]benzylphosphonate was orally administered in the rate of 50 mg/kg/day (administered as 5% arabic gum suspension).

After the tests were finished, the livers of rats in each one of the groups were enucleated, and the amounts of triglyceride and cholesterol in the liver were measured. The measurement was conducted by use of a commercially available enzymatic type kit after the lipid in the liver was extracted with a mixed solvent (chloroform:methanol=2:1).

Test results are shown in the following Table 1, wherein the asterisks (*) indicate significant differences ($p<0.01$) of the measured values of normal groups and test groups (the present invention) against the measured values of control groups by means of Student's test.

TABLE 1

| Group | Number of rats | Amount of triglycerides (mg/g of tissue) | Amount of cholesterol (mg/g of tissue) |
|---|---|---|---|
| Normal group | 9 | 28.59 ± 7.62(*) | 2.94 ± 0.25(*) |
| Control group | 6 | 91.98 ± 16.82 | 8.01 ± 1.13 |
| Test group | 6 | 59.70 ± 11.41(*) | 6.03 ± 1.13(*) |

As can be seen from Table 1, in the case of the rats kept by feeding with high fat diet, then as shown in the control group, amounts of triglycerides and cholesterol in the liver are increased so as to induce fatty liver. On the contrary, as clearly shown in the test group (the present invention), when the effective ingredient compound was administered, then amounts of triglycerides and cholesterol in the liver are remarkably inhibited. On the basis of these facts that the above-mentioned effective ingredient compound of the present invention capable to performs excellent effects for inhibiting the crisis of fatty liver and for improving fatty liver.

Pharmacological Test Example-2

[Test of the effect for improving fatty liver]

Wistar strain male rats of age in 9 weeks were kept for 3 days by feeding with a fructose-containing feed (containing 70% of fructose, 15% of casein, 7% of corn oil, 5% of mixture of minerals, 1% of mixture of vitamins and 2% of cellulose) so as to induce fatty liver in the rats.

The above-mentioned fatty liver-induced rats were administered orally with diethyl 4-[N-(4-bromo-2-cyanophenyl)carbamoyl]benzylphosphonate in the rate of 50 mg/kg once a day for 4 days (administered with in the form of 5% arabic gum suspension) (test group (the present invention group)).

4 Hours after the final administration with the effective ingredient compound, the liver of the rat was enucleated under anesthetized condition, then the amounts of neutral fats (triglycerides) and cholesterols in the liver were measured similarly as in Pharmacological test example-1.

The results are shown in the following Table 2. In the table, the fatty liver-induced rats which were administered without the effective ingredient compound of the present invention are defined as the control group and normal rats are defined as the normal group. The measured values of neutral fats and cholesterols in the livers are shown. The values indicated with the asterisks (*) and (**) show, respectively significant differences (p<0.05 and p<0.01), of the measured values of test groups (the present invention) against the measured values of control groups which were obtained by means of Student's test.

TABLE 2

| Group | Number of rats | Amount of triglycerides (mg/g of tissue) | Amount of cholesterol (mg/g of tissue) |
|---|---|---|---|
| Normal group | 8 | 20.69 ± 2.33 | 4.33 ± 0.40 |
| Control group | 8 | 46.15 ± 14.23 | 6.35 ± 1.20 |
| Test group | 8 | 33.25 ± 11.50(*) | 3.94 ± 0.66(**) |

As can be seen from Table 2, in accordance with the administration with the effective ingredient compound of the present invention (test group), there are clearly observed remarkable effects for decreasing triglycerides and cholesterols in the fatty liver-induced rats. On the basis of these facts, it is understood that the above-mentioned effective ingredient compounds of the present invention capable to perform excellently the effects for curing and improving of fatty liver.

Pharmacological Test Example-3

[Test of the effect for improving fatty liver]

In order to study the effect for improving fatty liver performed by various effective ingredient compound of the present invention, further pharmacological tests were conducted similarly as in Pharmacological test-2 by using the following compounds 1 to 4.

Compound 1:

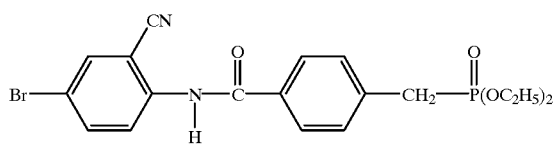

Compound 2:

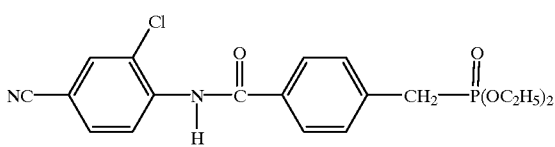

Compound 3:

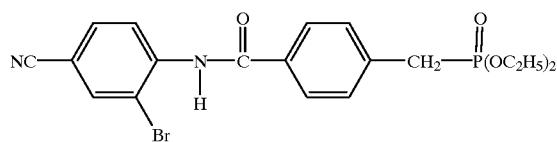

Compound 4:

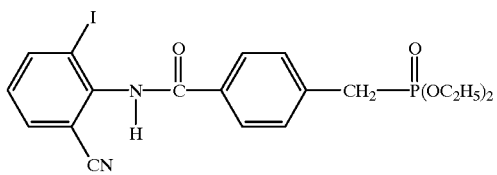

The results are shown in the following Table 3. In the table, there are disclosed the fatty liver-induced rats administered without the effective ingredient compound of the present invention are defined as the control group, while the normal rats are defined as the normal group, and the measured values of neutral fats and cholesterols in the liver are indicated, respectively. In Table 3, compound 1, i.e., diethyl 4-[N-(4-bromo-2-cyanophenyl)carbamoyl]benzylphosphonate is corresponding to the compound administered to the test group (the present invention), used in Table 2 of Pharmacological test example-2.

TABLE 3

| Group | Number of rats | Amount of triglycerides (mg/g of tissue) | Amount of cholesterols (mg/g of tissue) |
|---|---|---|---|
| Normal group | 6 | 22.38 ± 1.25 | 3.27 ± 0.78 |
| Control group | 6 | 46.59 ± 1.58 | 5.77 ± 0.54 |
| Test group | | | |
| Compound 1 | 6 | 29.00 ± 1.58 | 3.26 ± 0.67 |
| Compound 2 | 6 | 38.38 ± 5.92 | 3.97 ± 0.61 |
| Compound 3 | 6 | 34.86 ± 4.46 | 4.17 ± 0.44 |
| Compound 4 | 6 | 35.48 ± 7.29 | 4.19 ± 0.81 |

As can be seen from Table 3, there were observed remarkable effects for lowering triglycerides and cholesterols in the fatty liver-induced rats in the test group (the present invention) administered not only with compound 1 but also with compounds 2 to 4, respectively. Based on these facts that the above-mentioned effective ingredient compounds of the present invention can be able to perform excellent effects for curing and improving fatty liver.

Pharmacological Test Example-4

[Test of the effect for improving fatty liver]

To the caudal vein of Wistar strain male rats of age in 7 weeks, "streptozotocin" (manufactured by SIGMA) were administered in the rate of 85 mg/kg so as to induce diabetes mellitus.

The above-mentioned diabetes mellitus-induced rats were kept by feeding with solid feed (CRF-1, manufactured by Oriental Yeast Co., Ltd.) containing 0.25% of cholesterol for 8 months (control group).

As to the test group (the present invention), the rats were kept by feeding with the above-mentioned solid feed, and at the same time diethyl 4-[N-(4-bromo-2-cyanophenyl)carbamoyl]benzylphosphonate were orally administered, respectively in the rate of 30, 100 or 300 mg/kg/once a day for 8 months.

8 Months after that the test period was lapsed, the livers of the rats were enucleated and observed the states thereof and taken photographic pictures thereof.

Figure 2:
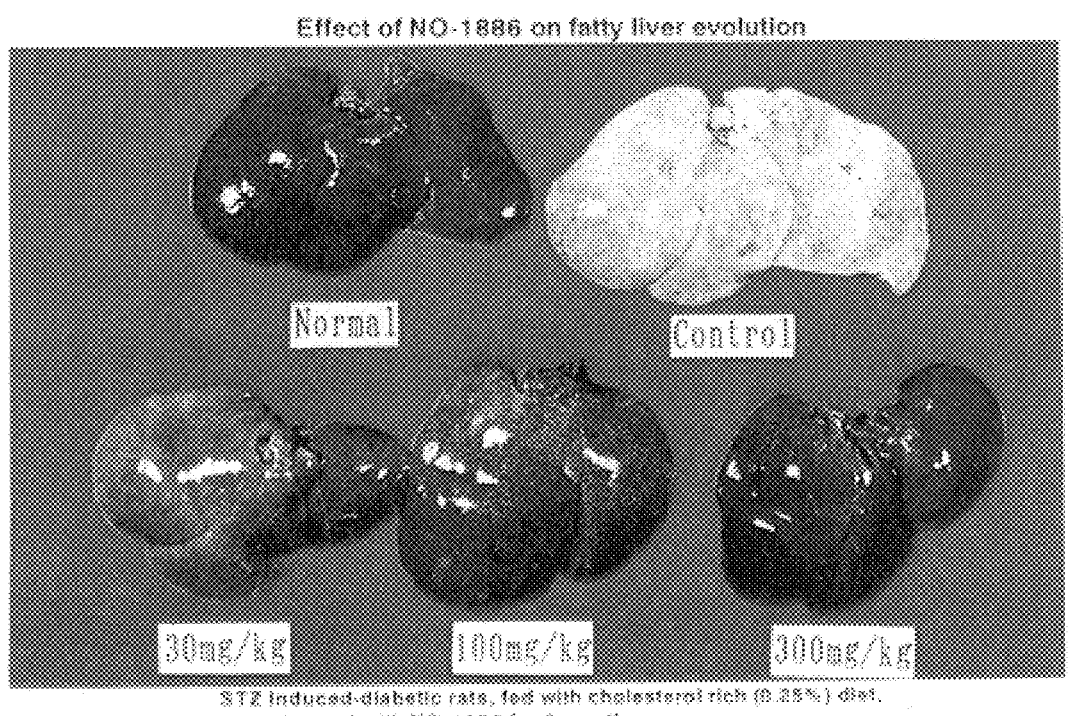

The results are shown in FIG. 1 and FIG. 2. FIG. 1 and FIG. 2 are substitute photographs for figures showing the actual states of enucleated livers. FIG. 1 is a monochrome (black and white) picture and FIG. 2 is a color picture.

In the Figures, "Normal" means, respectively the liver of rat (being kept by feeding with a normal diet) of the normal group. "Control" means, respectively the liver of rat of the control group. "30 mg/kg", "100 mg/kg" and "300 mg/kg", mean, respectively livers of rats of the test groups (the present invention) each of which were administered with the effective ingredient compound, respectively in the rate of "30 mg/kg", "100 mg/kg" and "300 mg/kg".

As can be seen from FIG. 1 and FIG. 2, although each one of the livers of test group (the present invention) is observed slightly lightening in color due to the accumulation of lipid therein depend on the concentration of the effective ingredient compound, each one of them, respectively shows similar color tone as compared with that of the liver of normal rat. On the contrary, the liver of rat in control group is observed remarkably whitened due to the accumulation of lipid, and the color tone is clearly different from that of the liver of rat in normal group. Thus, it is clearly understood that the above-mentioned effective ingredient compounds of the present invention are useful as agent for preventing and curing fatty liver.

Furthermore, hepatomegaly was not observed from the liver of rat in test group (the present invention).

Pharmacological Test Example 5

[Test of hemolysis]

Female ddY strain mice of age in 7 weeks were used to the test, and one group (test group) was consisting of 6 mice respectively. One of the effective ingredient compounds of the present invention (obtained in Preparation example 1) was suspended in 0.5% of carboxymethyl cellulose (CMC) solution and this suspension was compulsory administered orally by use of a peroral sonde in the rate of 600 mg/5 ml/kg for 10 days.

As to the control group, mice administered only with 0.5% of CMC solution without containing the effective ingredient compound were prepared.

After the final administration of the suspension, the test mice were fasted for 20 hours, then were subjected to dissect. The blood samples and the spleens were taken out. Numbers of erythrocytes in the blood were measured, and weight of the spleens were also measured.

As the result, the ratio of number of erythrocytes of test group being administered with the above-mentioned effective ingredient compound was 0.96 (in comparison with number of the erythrocytes of control group which was defined as 1), and the ratio of weight of the spleen of test group was 1.13 (similarly, in comparison with weight of the spleen of control group which was defined as 1). From both values, any significant difference was not recognized as compared with those shown by control group. On the basis of these facts that the effective ingredient compounds of the present invention do not show hemolysis as the side-effect.

Example of Pharmaceutical Preparation-1

[Preparation of tablet preparation]

The compound prepared by Preparation example 1 was shaped into tablets (1000 tablets, containing 250 mg of the compound per 1 tablet) by the following formulation.

| The compound prepared by | |
|---|---|
| Preparation example 1 | 250 g |
| Lactose (Japanese Pharmacopoeia grade) | 33.3 g |
| Corn starch (Japanese Pharmacopoeia grade) | 16.4 g |

| -continued | |
|---|---|
| The compound prepared by | |
| Calcium carboxymethyl cellulose (Japanese Pharmacopoeia grade) | 12.8 g |
| Methyl cellulose (Japanese Pharmacopoeia grade) | 6.0 g |
| Magnesium stearate (Japanese Pharmacopoeia grade) | 1.5 g |
| Total | 320.0 g |

In accordance with the above-mentioned formulation, the compound prepared by Preparation example-1, lactose, corn starch and calcium carboxymethyl cellulose were mixed sufficiently, the mixture thus obtained was granulated by use of an aqueous solution of methyl cellulose, the granules were passed through a sieve of 24 mesh, then mixed with magnesium stearate, then mixture was pressed into the shape of tablets by using a tablet machine.

Example of Pharmaceutical Preparation-2

[Preparation of capsule preparation]

Diethyl 4-[N-(2-chloro-4-cyanophenyl)carbamoyl]-benzylphosphonate as the effective ingredient compound was shaped into hard gelatin capsule preparations (1,000 capsules, containing 250 mg of the compound per 1 capsule) by the following formulation.

| Diethyl 4-[N-(2-chloro-4-cyanophenyl)-carbamoyl]benzylphosphonate | 250 g |
|---|---|
| Crystalline cellulose (Japanese Pharmacopoeia grade) | 30 g |
| Corn starch (Japanese Pharmacopoeia grade) | 17 g |
| Talc (Japanese Pharmacopoeia grade) | 2 g |
| Magnesium stearate (Japanese Pharmacopoeia grade) | 1 g |
| Total | 300 g |

In accordance with the above-mentioned formulation, each one of the ingredients was finely powdered and mixed together sufficiently so as to obtain a uniform mixture, then thus obtained mixture was filled in gelatin capsules for oral administration having the desired size to prepare the objective capsule preparations.

Example of Pharmaceutical Preparation-3

[Preparation of granular preparation]

Diethyl 4-[N-bromo-2-cyanophenyl)carbamoyl]-benzylphosphonate as the effective ingredient compound was shaped into granular preparations (1,000 g, containing 500 mg of the compound per 1 g) by the following formulation.

| Diethyl 4-[N-(4-bromo-2-cyanophenyl)-carbamoyl]benzylphosphonate | 500 g |
|---|---|
| Corn starch (Japanese Pharmacopoeia grade) | 250 g |
| Lactose (Japanese Pharmacopoeia grade) | 100 g |
| Crystalline cellulose (Japanese Pharmacopoeia grade) | 100 g |
| Calcium carboxymethyl cellulose (Japanese Pharmacopoeia grade) | 40 g |
| Hydroxypropylcellulose (Japanese Pharmacopoeia grade) | 10 g |
| Total | 1,000 g |

In accordance with the above-mentioned formulation, compound of the effective ingredient, corn starch, lactose, crystalline cellulose and calcium carboxymethyl cellulose

What is claimed is:

1. A method for preventing and curing fatty liver by administering to a patient in need thereof, an agent for preventing and curing fatty liver containing, as the effective ingredient, a carboxylic acid amide derivative represented by the general formula (1),

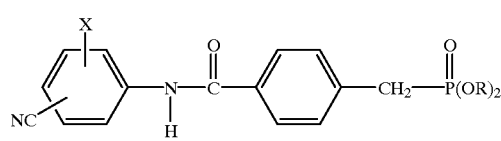
(1)

(wherein R is a lower alkyl group; and X is a halogen atom).

2. The method for preventing and curing fatty liver according to claim 1, wherein the effective ingredient compound is a carboxylic acid amide derivative represented by the general formula (1a),

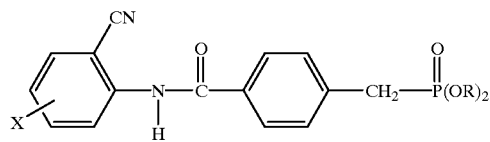
(1a)

(wherein R and X are the same as defined in the above).

3. The method for preventing and curing fatty liver according to claim 1, wherein the effective ingredient compound is a carboxylic acid amide derivative represented by the general formula (1b),

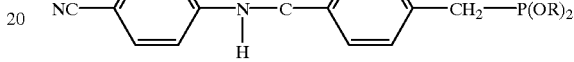
(1b)

(wherein R and X are the same as defined in the above).

4. The method for preventing and curing fatty liver according to claim 1, wherein the effective ingredient compound is diethyl 4-[N-(4-bromo-2-cyanophenyl) carbamoyl]-benzylphosphonate.

* * * * *